United States Patent [19]

Brumfield

[11] 4,212,741
[45] Jul. 15, 1980

[54] BLOOD PROCESSING APPARATUS

[76] Inventor: Robert C. Brumfield, 455 S. Oakland Ave., Pasadena, Calif. 91101

[21] Appl. No.: 895,237

[22] Filed: Apr. 10, 1978

[51] Int. Cl.² .................. B01D 31/00; B01D 33/06; A61M 1/03
[52] U.S. Cl. .................. 210/241; 210/321 B; 210/358; 210/365; 422/48
[58] Field of Search .................. 210/321 B, DIG. 23, 210/22, 241, 326, 329, 358, 365, 367, 321 A; 128/214 B; 422/45, 46, 48

[56] References Cited

U.S. PATENT DOCUMENTS

| 3,026,871 | 3/1962 | Thomas | 128/DIG. 3 |
| 3,479,280 | 11/1969 | Boissevain | 210/321 B |
| 3,771,658 | 11/1973 | Brumfield | 210/186 |

Primary Examiner—Charles N. Hart
Assistant Examiner—David Sadowski

[57] ABSTRACT

The disclosure sets forth blood processing apparatus of the general type which employs a cylindrical rotor with a semi-permeable membrane at its outer surface, rotatable within a surrounding stationary casing or housing, blood being supplied and discharged at angularly spaced loci of the casing, a secondary fluid being supplied to the interior of the rotor, effecting a cross-transfer of a component in the blood, and a secondary fluid, or a component thereof, across the membrane, sometimes referred to as a "journal machine" to distinguish such type from others which differ basically therefrom. The basic environment is like that of certain patents, identified hereinafter, and incorporates, by reference, features thereof insofar as they are applicable to the present disclosure. The improvements disclosed over such prior art include a membrane configuration and manner of supporting same, an openable housing construction and movable mount therefor, a secondary fluid communication connection with a hollow rotor shaft, an alternative form of housing peripheral configuration, and others to hereinafter appear. Also, as will subsequently appear, certain of the exemplary structural improvements provide novel operational differences resulting in novel blood processing, also contemplated within the purview thereof.

13 Claims, 10 Drawing Figures

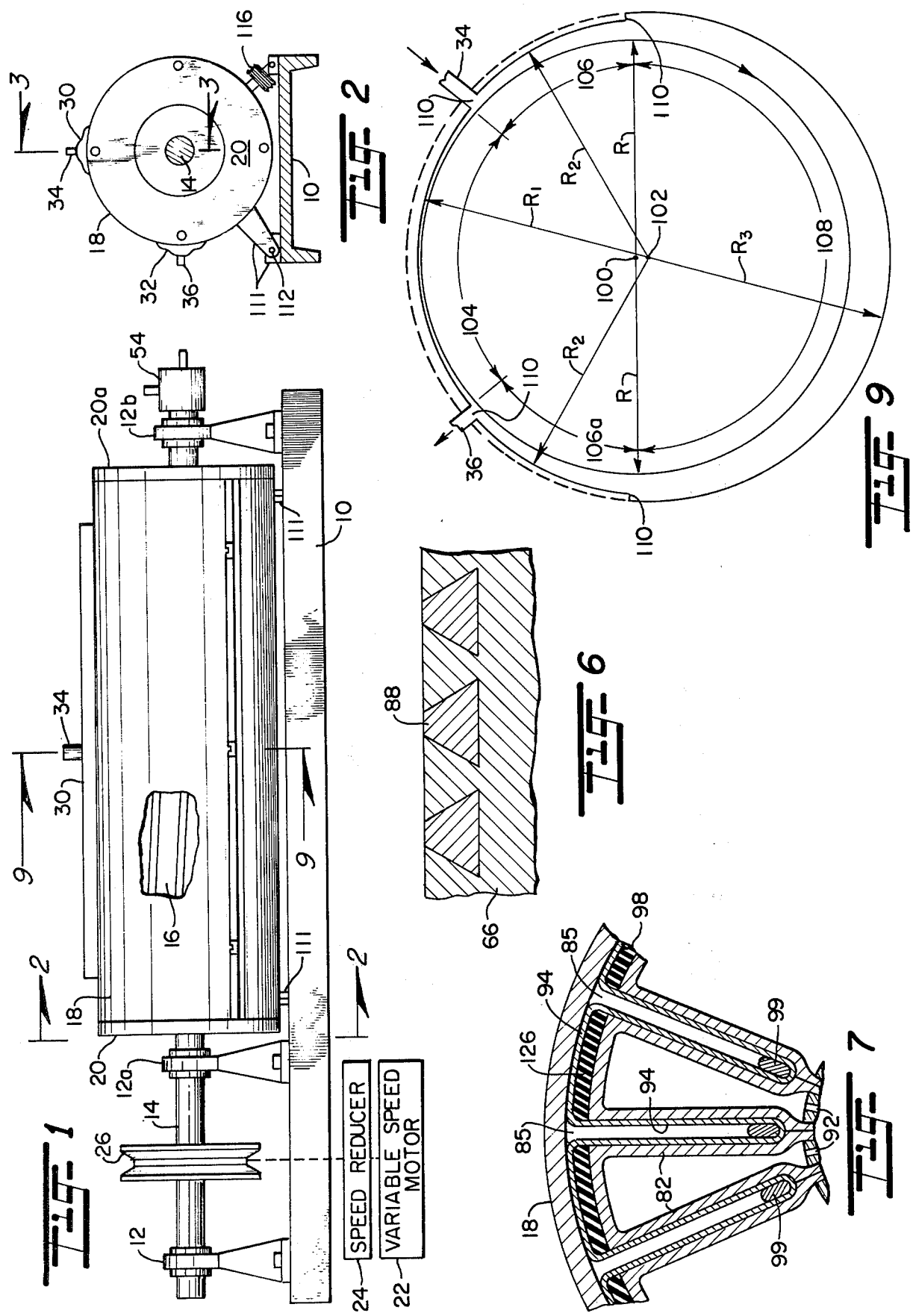

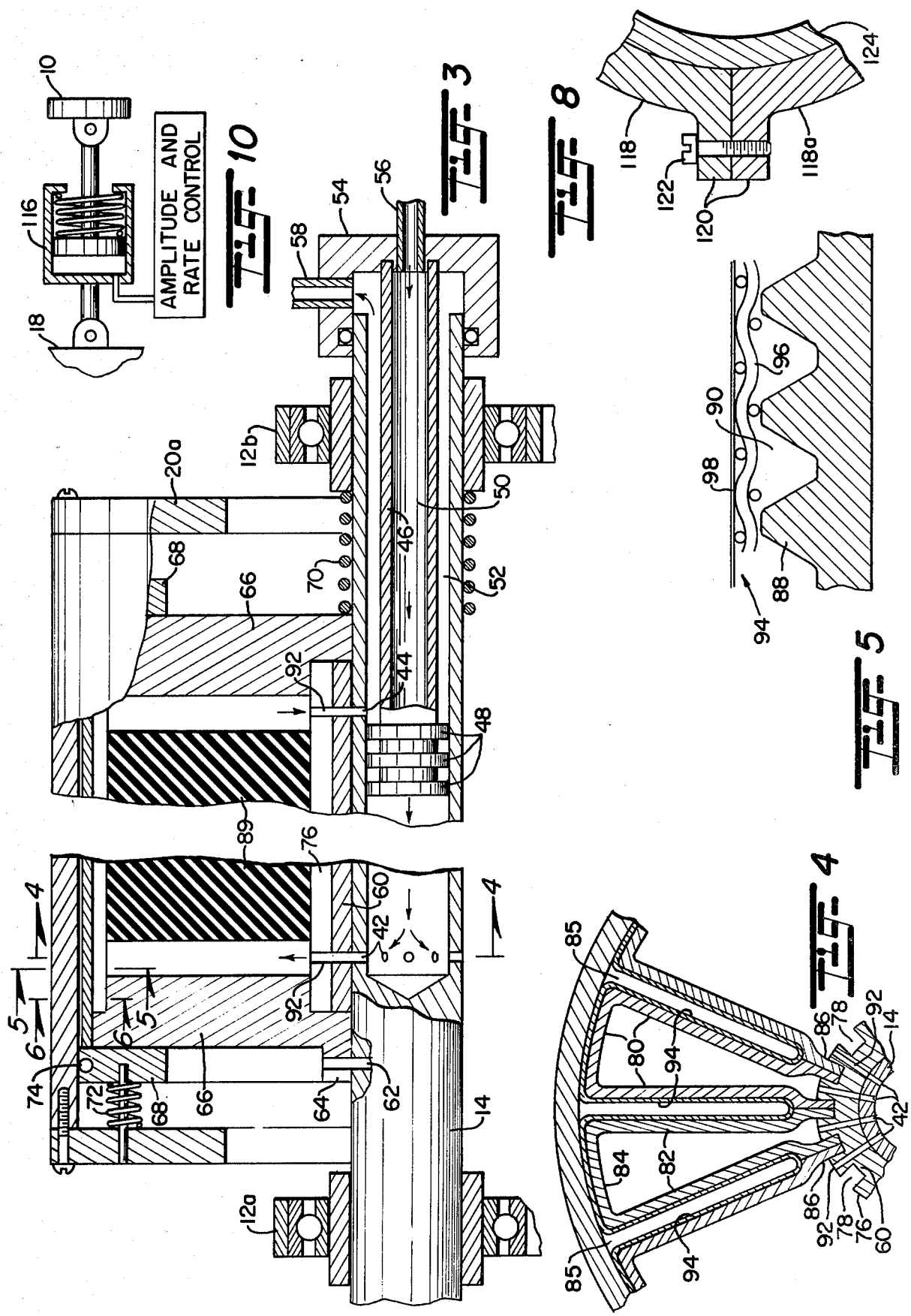

BLOOD PROCESSING APPARATUS

BACKGROUND OF THE INVENTION

During certain medical procedures, such as radical cardio pulmonary surgery, it is conventional practice to remove venous blood from a patient, pass it through apparatus, and return same as arterial blood, the apparatus simulating the function of the human lungs to remove, principally, carbon dioxide from the blood and add oxygen thereto. Also, it may serve as a pump to provide a differential pressure between inlet venous blood and outlet arterial blood. Further, by choice of a suitable fluid supplied to the apparatus, it may serve for blood dialysis, simulating the function if kidneys, in instances of renal failure. Such apparatus has been fabricated in various forms among which include the apparatus disclosed in U.S. Pat. Nos. 3,771,658 and 3,771,899, both of which have issued to Robert C. Brumfield. Briefly, such apparatus comprises a cylindrical rotor having a semi-permeable membrane at its peripheral surface, which is mounted eccentrically in a surrounding cylindrical housing, means for supplying blood to the space therebetween for residence with the membrane, and means for supplying a secondary fluid, such as oxygen or a dialysis liquid, to the interior of the rotor. The second patent differs from the first principally in that the rotor is also mounted eccentrically on its drive shaft which effects a pulsating pumping pressure, rather than a constant pumping pressure. Other art is also disclosed in patent application Ser. No. 894,023 of Allen C. Billmeyer for Blood Processing Apparatus (filed concurrently herewith) which relates to an improvement on the patents referred to in that the rotor is formed with angularly spaced ribs, forming flutes therebetween, which materially increase the mass transfer area, as compared to a right circular cylinder of the same diameter and length having a membrane only at its outer cylindrical envelope surface.

SUMMARY OF THE INVENTION

The present invention relates, in most aspects, to various improvements over the Brumfield patents previously referred to, and in some aspects, to improvements over the Billmeyer application also referred to. Such improvements comprise: A readily removable dual conduit tube insertable in one end of the hollow rotor shaft for delivering and discharging fluid to and from distal and proximate communication ports in the rotor shaft; a movable mount for the casing for adjusting its eccentricity relative to the rotor or for continuously moving the casing with variable amplitude and at variable rate to simulate the like action of a human heart; a resilient backing for the membrane for flexing same to facilitate the transfer of fluid components therethrough; a split casing adapted to be opened to facilitate access to the rotor shaft and to facilitate removal and replacement of the rotor from and onto the rotor shaft; and alternative form of casing provided with stepped transitions therein between different peripheral blood treating zones; a readily replaceable unitary discardable rotor; a fluted support structure for a membrane, various details thereof including an alternative helical configuration thereof and details of retaining the membrane affixed to the supports; and processes of treating blood.

The foregoing briefly recited features also comprise the principal objects of the invention.

Further objects, advantages, and salient features will become more apparent from the detailed description to follow, the appended claims, and the accompanying drawing to now be briefly described.

FIG. 1 is a broken away side elevation of a general environment which may embody the various features of the invention;

FIG. 2 is a section taken on line 2—2, FIG. 1;

FIG. 3 is an enlarged longitudinal central section taken on line 3—3, FIG. 2, a central portion being broken away;

FIG. 4 is a section taken on line 4—4, FIG. 3; certain details being omitted;

FIG. 5 is a greatly enlarged section taken on line 5—5, FIG. 3 illustrating the omitted details in FIG. 4;

FIG. 6 is a like section taken on line 6—6, FIG. 3;

FIG. 7 is a section, like FIG. 4, illustrating an alternative form thereof, in which a resilient cushion underlies the rotor membrane;

FIG. 8 is a transverse section through the casing illustrating an alternative form of the invention, employing a casing liner;

FIG. 9 is a diagrammatic cross section, taken on line 9—9, FIG. 1, illustrating an alternative form of casing inner surface; and FIG. 10 is an enlargement of a detail of FIG. 2.

DETAILED DESCRIPTION OF PREFERRED EMBODIMENTS

General

Referring now to the drawing in detail, and first to FIGS. 1 and 2, the subject of the invention comprises in general, a suitable base or frame 10, bearings 12,12a,12b secured thereto, a rotor shaft 14 supported by the bearings which rotatably supports a rotor 16, the rotor being surrounded by a cylindrical casing or housing 18 supported by the base, including end rings 20,20a. The rotor shaft may be power driven by a variable speed motor 22 and speed reducer 24, through a belt (not shown) coupled to pulley 26 secured to the rotor shaft. Blood supply and discharge conduits 30,32 respectively, are affixed to the casing, extending longitudinally thereof substantially along its length and parallel with the rotor axis, to which are affixed centrally thereof, inlet and outlet connectors 34,36 which may be connected by hoses (not shown) to the blood circulatory system of a patient.

Secondary Fluid Supply

As best shown in FIG. 3, rotor shaft 14 is partially hollow and provided with inlet apertures 42 and outlet apertures 44 which communicate the hollow portion with ends of the rotor, to be subsequently described in detail. A tubular member or pizal 46 is removably insertable into the right end of the rotor shaft, its distal or left end sealingly engaging the hollow rotor shaft at a locus between apertures 42,44. As illustrated, the sealing means comprises a plurality of annular rings 48 which closely fit the rotor shaft bore and provide a labyrinth seal between opposite ends of the rings. The pizal is tubular, providing a central channel 50 and an annular surrounding channel 52. As will be apparent, a secondary fluid, such as oxygen or a dialysate may be delivered to the bore of the pizal, flow through same to apertures 42, thence to the left end of the rotor, through the length of the rotor, and be discharged through apertures 44 to annular channel 52. A suitable stationary fitting or gland 54 sealingly engages the right end of the rotor shaft and is so constructed to communicate the pizal bore and annular channel surrounding same with hose fittings 56,58 connected to a secondary fluid source (not shown).

Rotor

The replaceable and normally disposable rotor 16 comprises, in general, a tube 60 which slideably engages the rotor shaft and is driven by same with a pin 62 secured to the rotor shaft which engages within a slot 64 in left end closure 66. End closures 66,66 are affixed to the tube and engage seals 68,68 carried by the casing which prevents radially inward leakage of blood from the space between the rotor periphery and inside surface of the casing. These may be of any suitable form, such as rings which engage the end closures 66 and springs 72 which axially and resiliently urge them into sealing engagement with an end closure. An O-ring 74 in each ring 68 prevents axial leakage along the inner surface of the casing. Since the specific seals form no part, per se, of the present invention, other seals may be employed, such as disclosed in the Brumfield patents, previously referred to.

Tube 60, as best shown in FIG. 4, is provided with splines 76, forming slots 78 therebetween, which receive membrane supports 80. Each support 80 is formed as an extrusion having side walls 82, a connecting lobe 84 and inner or root ends 86 which fit within the slots, the inner ends abutting like ends of an adjacent support. The outer surfaces of walls 82 and lobes 84 are provided with longitudinally extending ribs 88, shown in FIG. 5, which form channels 90 therebetween for flow of the secondary fluid along same. Except near opposite ends of supports 80, they are filled with closed cell foam filler 89, or like material, to prevent longitudinal flow of the secondary fluid between walls 82. The angularly spaced supports 80 may be secured to the splined shaft in suitable manner, such as by cement (not shown). At each end of a support 80, its wall is cut away, leaving only ribs 88, the spaces between which form fluid channels 90. As shown in FIG. 6, each end closure 66, previously referred to, is formed as a potting material in which the ends of the ribs are embedded. Angularly spaced apertures 92 are provided in tube 60 which communicate with apertures 42, 44 in shaft 14, communicating the space between walls 82 of each member adjacent its ends with the bore of the shaft. The fluid thence flows between the ribs, at their cut-away ends, and into the longitudinal channels 90 formed therebetween and along the outer surfaces of walls 82 and lobes 84.

The assembled support structure (FIG. 4) is covered with a thin membrane to now be described. Referring to FIG. 5, covering 94 comprises woven screen 96 and an overlying thin sheet 98 of membrane material, such as polycarbonate, which may be of the thickness of the order of 0.001", thus being fragile and requiring suitable support, which, as will be apparent, is provided by the screen. The membrane and screen are secured together in suitable manner, such as by cement or heat seals (not shown), and the assembly secured in like manner to ribs 88. Alternatively, as shown in FIG. 7, the membrane may be disposed around the supports and successively folded into blood carrying slots 85 and secured therein by longitudinal bars 99 disposed adjacent the bottoms of the slots which may thence be locked in any suitable manner, such as by cement.

In addition to the exemplary manners of applying the covering 94 to the supports, as just described, supports 80 may be individually covered with the material and secured by cement and the covered supports may then be assembled on the shaft and secured thereto by cement or other securing means.

Alternatives

As previously alluded to, the present invention may incorporate, as applicable, the prior art features of the Brumfield patents wherein the axes of rotor and casing are offset to provide an eccentric blood space surrounding the rotor to effect constant differential pumping pressure between the casing blood inlet and outlet; also, the feature of a rotor, the periphery of which rotates eccentrically with respect to the rotor axis to effect pulsating differential pumping pressure. Other variants are also within the purview of the present improvements, to now be described.

Stepped Casing

As so far described, the internal surface of the casing is formed as the surface of a right circular cylinder. FIG. 9 illustrates an alternative form of such shape wherein the rotor rotates about axis 100 and the casing surface is defined by several radii rotated about a point 102, offset from axis 100. Thus, radius $R_1$ is slightly greater than radius R of the rotor to form an arcuate sealing zone 104 between the blood inlet and outlet. Radius $R_2$, greater than radius $R_1$, then forms an arcuate pumping zone 106. Radius $R_3$, greater than radius $R_2$, then forms a mixing zone 108. The radius then decreases to $R_2$ forming a second pumping zone, terminating at outlet 36. As will be apparent, each of the zones is eccentric to the rotor axis and, since their radii differ, form discrete steps 110 therebetween. As distinguished from a gradual decrease or increase in the radial width of the blood space, as in the prior art, which, in effect, results in relatively longer arcuate transition zones therebetween, the transition zones are more abrupt, thus, in effect, increasing the arcuate length of each discrete zone as compared to a cylindrical case of the same diameter.

Resilient Rotor Lobes

FIG. 7 is like FIG. 4 (further details of which are shown in FIG. 5) illustrating membrane 94 which overlies ribs 88 on all exterior surfaces of supports 80. It differs from such structure, however, in that a strip 126 of porous resilient material, such as reticulated urethane, is disposed between the ribs and covering 94 at each support lobe. The inner surface of casing 18 may be concentric with the rotor axis and proportioned so that the membrane lobes resiliently wipe along same throughout their rotation. If a pumping action is desired, however, the casing inner surface may be disposed eccentric to the rotor axis so that the resilient wiping occurs only at the arcuate sealing zone between the blood inlet and outlet, the lobes clearing the casing during the remaining portion of a revolution. In either construction, along the wiping zone, the blood film is subjected to shear, straining or distorting the red blood corpuscles and effecting, through such strain, increased mass transfer thereto or therefrom. Also, since the membrane is strained, principally in flexure, the mass transfer therethrough is increased as compared with an unstrained membrane. Preferably, the surface of the casing should be hydrophilic, that is, remain wetted. While the resilient lobe feature has been illustrated in connection with blood carrying slots 85 for simplification of the disclosure, it will become apparent that the slots may be omitted in which event, the resilient material 126 may cover the entire periphery of the rotor.

Casing Mount

As illustrated in FIG. 2, casing 18 is supported by hinges 111, preferably near its ends, one of which is shown, to permit the casing to be moved about a hinge axis 112 parallel with the rotor axis which varies the eccentric radial blood space between the rotor periphery and inside surface of the casing. An eccentricity control device 116, pivotally connected at its ends to casing 18 and base 10, provides means for adjusting such eccentricity. In its most simple form, device 116 may be a turnbuckle or other adjustable strut for adjusting the eccentricity to a desired value.

Device 116 may, however, be in the form of a reciprocable motor with variable stroke, such as a bellows, double acting hydraulic actuator, variable stroke eccentric mechanism, etc., which may be operated to swing the casing about its hinge axis in desired amplitude, as illustrated in FIG. 11. Also, as will be apparent, its rate of oscillation may be varied, thus effecting cyclic change of the eccentric blood space in both amplitude and rate. Thus, by suitable choice of the two variables, the apparatus may be adjusted to serve as a pump and simulate pressure of heart pulses and rate thereof.

Split Casing and Liner

Casing 18, in its most simple form, may be formed as hereinbefore described as an integral cylinder. A refinement of such construction, however, is illustrated in FIGS. 2 and 8 wherein it is formed in two halves 118,118a which are secured together in any suitable manner, such as by flanges 120 and locking means, such as screws 122, thus forming a clamshell-like structure which permits improved access to its interior and to the rotor. With this construction a readily replaceable cylindrical liner 124 may be employed which may be slid over the rotor, after replacing same, and the two halves clamped together around the liner, retaining the latter affixed to the casing.

What I claim is:

1. In blood treating apparatus of the type having a rotor with peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements in combination comprising;
   (a) said third means including a hollow shaft rotatably supporting the rotor,
   (b) means for delivering said second fluid to one end of said shaft for axial flow through the rotor, and
   (c) means for discharging said second fluid from the same end of said shaft after flowing through the rotor.

2. Apparatus in accordance with claim 1 wherein said shaft is provided with an open accessible bore at said end, axially spaced distal and proximate conduits in the shaft for supplying the second fluid to the rotor and discharging same therefrom, a tubular member insertable into said bore at said end having a fluid sealing distal end adapted to be disposed in said bore and between said conduits, said tubular member also providing an annular space therearound,
   (a) the bore of said tubular member communicating with the distal conduit and the annular space communicating with the proximate conduit,
   (b) the bore of the tubular member and the annular space surrounding same forming conduits for the second fluid for axial flow through the rotor.

3. Apparatus in accordance with claim 2 wherein said fluid sealing distal end comprises a plurality of axially spaced rings on said tubular member closely rotatably fitting the bore of the shaft and forming a labyrinth seal to prevent flow of the second fluid axially between ends of the rings.

4. Apparatus in accordance with claim 2 including a sealing gland device disposed at the outer end of said tubular member constructed to sealingly engage an end of said shaft, and apertures extending therethrough for communicating a source of said second fluid with its bore and the annular space surrounding same.

5. In blood treating apparatus of the type having a rotor with a peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements, in combination, comprising;
   (a) said casing and rotor having longitudinal parallel axes adapted to be relatively moved between a position in which they are coincident, providing an annular space of uniform width between the rotor periphery and inner surface of the casing, and other positions wherein the axes are spaced, providing an eccentric space therebetween, wherein the rotor is mounted for rotation about a fixed axis and the casing is pivotally mounted about an axis disposed parallel to the rotor and casing axes in a position to effect minimum eccentricity between the casing and rotor along an axial zone between said first and second loci.

6. Apparatus in accordance with claim 5 wherein said axial zone is substantially midway between said first and second loci.

7. In blood treating apparatus of the type having a rotor with a peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements, in combination, comprising;
   (a) said casing and rotor having longitudinal parallel axes adapted to be relatively moved between a position in which they are coincident, providing an annular space of uniform width between the rotor periphery and inner surface of the casing, and other positions wherein the axes are spaced, providing an eccentric space therebetween, wherein the moving means is constructed to cyclically relatively move said axes in varying desired amplitude and rate, whereby amplitude of pressure pulses and rate thereof may be selected to simulate that of a human heart.

8. Apparatus in accordance with claim 7 wherein the moving means comprises a reciprocating variable speed motor having a selectively variable stroke.

9. Apparatus in accordance with claim 7 wherein the rotor is mounted for rotation about a fixed axis and the casing is pivotally mounted.

10. In blood treating apparatus of the type having a rotor with peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements, in combination, comprising;
 (a) said casing being so shaped, in the direction of rotor rotation, to provide an arcuate sealing zone of minimum width around the rotor between said second and first loci;
 (b) the casing thence being discretely outwardly radially stepped to provide a first arcuate pumping zone of gradually increasing width;
 (c) the casing thence being discretely outwardly radially stepped to provide an arcuate mixing zone of gradually increasing width toward its midpoint and thence of like gradually decreasing width toward the end thereof;
 (d) the casing thence being discretely inwardly radially stepped a provide a second arcuate pumping zone of gradually decreasing width toward said second locus; and
 (e) the casing thence being discretely inwardly radially stepped to form one end of said sealing zone
 (f) the various zones are formed as circular arcs about a common axis spaced from the rotor axis and wherein the radii of the pumping zones is greater than that of the sealing zone and the radius of the mixing zone is greater than that of the pumping zones.

11. In blood treating apparatus of the type having a rotor with peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements, in combination, comprising;
 (a) said casing being so shaped, in the direction of rotor rotation, to provide an arcuate sealing zone of minimum width around the rotor between said second and first loci;
 (b) the casing thence being discretely outwardly radially stepped to provide a first arcuate pumping zone of gradually increasing width;
 (c) the casing thence being discretely outwardly radially stepped to provide an arcuate mixing zone of gradually increasing width toward its midpoint and thence of like gradually decreasing width toward the end thereof;
 (d) the casing thence being discretely inwardly radially stepped to provide a second arcuate pumping zone of gradually decreasing width toward said second locus; and
 (e) the casing thence being discretely inwardly radially stepped to form one end of said sealing zone
 (f) the periphery of the rotor is eccentric to the rotor axis, to thereby effect pulsating pumping pressure.

12. In blood treating apparatus of the type having a rotor with peripheral wall through which mass transfer may occur and journaled for rotation in a surrounding casing, first means for supplying blood to the interior of the casing at a first locus, second means for discharging the blood from the casing at a second locus after a desired angular residence with the rotor, and third means for supplying a second fluid, such as oxygen or a dialysate, to the interior of the rotor, the improvements, in combination, comprising;
 (a) said rotor and wall comprising a rigid rotary support, juxtaposed porous resilient cushion means overlying the support, and a juxtaposed thin flexible membrane overlying the cushion means, the construction being such that the membrane may resiliently wipe along the inner surface of the casing, during at least a portion of its revolution, and subject blood in contact therewith to a shearing action to facilitate means transfer from or to red blood corpuscles therein, the porosity of the cushion member being such that the second fluid may be delivered therethrough and into contact with the inner surface of the membrane.

13. Apparatus in accordance with claim 12 wherein said rotary support comprises a plurality of angularly spaced members, each having a lobe at its outer end, and forming blood carrying slots between the spaced members, each lobe having the cushion means overlying same, whereby said shearing action occurs only at the lobes and between the blood carrying slots.

* * * * *